(12) United States Patent
Zhang et al.

(10) Patent No.: US 10,633,432 B2
(45) Date of Patent: Apr. 28, 2020

(54) VC-CAR MOLECULE AND USE THEREOF IN REMOVING HIV-1 INFECTED CELLS

(71) Applicant: Shenzhen City of Regeneration Biological Pharmaceutical Technology Co., Ltd., Shenzhen (CN)

(72) Inventors: Hui Zhang, Guangdong (CN); Bingfeng Liu, Guangdong (CN); Fan Zou, Guangdong (CN)

(73) Assignee: Shenzhen City of Regeneration Biological Pharmaceutical Technology Co., Ltd., Shenzhen (CN)

( * ) Notice: Subject to any disclaimer, the term of this patent is extended or adjusted under 35 U.S.C. 154(b) by 0 days.

(21) Appl. No.: 16/322,470

(22) PCT Filed: Jan. 23, 2017

(86) PCT No.: PCT/CN2017/072266
§ 371 (c)(1),
(2) Date: Jan. 31, 2019

(87) PCT Pub. No.: WO2018/028157
PCT Pub. Date: Feb. 15, 2018

(65) Prior Publication Data
US 2019/0367587 A1   Dec. 5, 2019

(30) Foreign Application Priority Data

Aug. 10, 2016 (CN) .......................... 2016 1 0652995

(51) Int. Cl.
| | |
|---|---|
| C07K 16/10 | (2006.01) |
| A61K 39/00 | (2006.01) |
| A61K 39/21 | (2006.01) |
| A61K 39/42 | (2006.01) |
| A61K 39/12 | (2006.01) |
| C07K 14/725 | (2006.01) |
| C07K 14/705 | (2006.01) |
| C12N 5/0783 | (2010.01) |
| C12N 7/00 | (2006.01) |

(52) U.S. Cl.
CPC ...... *C07K 16/1063* (2013.01); *C07K 14/7051* (2013.01); *C07K 14/70521* (2013.01); *C07K 14/70578* (2013.01); *C12N 5/0636* (2013.01); *C12N 7/00* (2013.01); *C07K 2317/622* (2013.01); *C07K 2317/76* (2013.01); *C07K 2319/02* (2013.01); *C07K 2319/03* (2013.01); *C07K 2319/30* (2013.01); *C07K 2319/33* (2013.01); *C12N 2501/2302* (2013.01); *C12N 2501/2307* (2013.01); *C12N 2740/16111* (2013.01)

(58) Field of Classification Search
CPC ............ C07K 2317/76; C07K 16/1063; C07K 2317/565; C07K 2317/21; A61K 2039/505
See application file for complete search history.

(56) References Cited

FOREIGN PATENT DOCUMENTS

| | | | |
|---|---|---|---|
| CN | 103483453 | * | 1/2014 |
| CN | 103502438 | | 1/2014 |
| CN | 105518143 | | 4/2016 |
| CN | 106279432 | | 1/2017 |
| WO | 2015084859 | | 6/2015 |

OTHER PUBLICATIONS

"International Search Report (Form PCT/ISA/210)" dated May 15, 2017, with English translation thereof, pp. 1-4.

* cited by examiner

*Primary Examiner* — Barry A Chestnut
(74) *Attorney, Agent, or Firm* — JCIPRNET

(57) ABSTRACT

The present invention relates to a VC-CAR molecule and a use thereof in removing HIV-1 infected cells. The VC-CAR molecule is characterized by linking an HIV-1 broad-spectrum neutralizing antibody VRC01 sourced scFv sequence and an intracellular domain sequence of a conventional CAR molecule which are respectively used as extracellular and intracellular domains. A T cell modified by the VC-CAR molecule can be specifically activated and secrete a great number of cytotoxicity-related cytokines, so that lysis of a target cell can be powerfully mediated, and it can be better used for anti-infection adoptive immunotherapy.

14 Claims, 5 Drawing Sheets
Specification includes a Sequence Listing.

```
                              SEQUENCE LISTING

<160> NUMBER OF SEQ ID NOS: 4

<210> SEQ ID NO 1
<211> LENGTH: 735
<212> TYPE: DNA
<213> ORGANISM: Artificial Sequence
<220> FEATURE:
<223> OTHER INFORMATION: Synthesized polynucleotide from HIV-1 broad-
      spectrum neutralizing antibody VRC01 sourced scFv sequence

<400> SEQUENCE: 1
atggaaattg tgttgacaca gtctccaggc accctgtctt tgtctccagg ggaaacagcc      60
atcatctctt gtcggaccag tcagtatggt tccttagcct ggtatcaaca gaggcccggc     120
caggccccca ggctcgtcat ctattcgggc tctactcggg ccgctggcat cccagacagg     180
ttcagcggca gtcggtgggg gccagactac aatctcacca tcagcaacct ggagtcggga     240
gattttggtg tttattattg ccagcagtat gaattttttg gccaggggac caaggtccag     300
gtcgacatta agcgagaggg cagaggaagt ctgctaacat gcggtgacgt cgaggagaat     360
cctggccagg tgcagctggt gcagtctggg ggtcagatga agaagcctgg cgagtcgatg     420
agaatttctt gtcgggcttc tggatatgaa tttattgatt gtacgctaaa ttggattcgt     480
ctggcccccg gaaaaaggcc tgagtggatg ggatggctga agcctcgggg gggggccgtc     540
aactacgcac gtccacttca gggcagagtg accatgactc gagacgttta ttccgacaca     600 gccttttttgg agctgcgctc gttgacagta gacgacacgg ccgtctactt ttgtactagg     660
ggaaaaaact gtgattacaa ttgggacttc gaacactggg gccggggcac cccggtcatc     720
gtctcatcag aattc                                                      735

<210> SEQ ID NO 2
<211> LENGTH: 1656
<212> TYPE: DNA
<213> ORGANISM: Artificial Sequence
<220> FEATURE:
<223> OTHER INFORMATION: Synthesized polynucleotide including SEQ ID
      NO:1 and third generation CAR structure

<400> SEQUENCE: 2
atggaaattg tgttgacaca gtctccaggc accctgtctt tgtctccagg ggaaacagcc      60
```

```
atcatctctt gtcggaccag tcagtatggt tccttagcct ggtatcaaca gaggcccggc    120
caggccccca ggctcgtcat ctattcgggc tctactcggg ccgctggcat cccagacagg    180
ttcagcggca gtcggtgggg gccagactac aatctcacca tcagcaacct ggagtcggga    240
gattttggtg tttattattg ccagcagtat gaatttttg gccaggggac caaggtccag     300
gtcgacatta agcgagaggg cagaggaagt ctgctaacat gcggtgacgt cgaggagaat    360
cctggccagg tgcagctggt gcagtctggg ggtcagatga agaagcctgg cgagtcgatg    420
agaatttctt gtcgggcttc tggatatgaa tttattgatt gtacgctaaa ttggattcgt    480
ctggcccccg gaaaaaggcc tgagtggatg ggatggctga agcctcgggg ggggccgtc     540 aactacgcac gtccacttca gggcagagtg accatgactc gagacgttta ttccgacaca    600 gccttttttgg agctgcgctc gttgacagta gacgacacgg ccgtctactt ttgtactagg   660
ggaaaaaact gtgattacaa ttgggacttc gaacactggg gccggggcac cccggtcatc    720
gtctcatcag aattcggtgg aggcggttca ggcggaggtg gctctggcgg tggcggatcg    780
ttcgtgccgg tcttcctgcc agcgaagccc accacgacgc cagcgccgcg accaccaaca    840
ccggcgccca ccatcgcgtc gcagcccctg tccctgcgcc cagaggcgtg ccggccagcg    900
gcggggggcg cagtgcacac gagggggctg gacttcgcct gtgatatcta catctgggcg    960
cccttggccg ggacttgtgg ggtccttctc ctgtcactgg ttatcaccct ttactgcaac   1020
cacaggaaca ggagtaagag gagcaggctc ctgcacagtg actacatgaa catgactccc   1080
cgccgccccg ggcccacccg caagcattac cagccctatg ccccaccacg cgacttcgca   1140
gcctatcgct cccgtttctc tgttgttaaa cggggcagaa agaagctcct gtatatattc   1200
aaacaaccat ttatgagacc agtacaaact actcaagagg aagatggctg tagctgccga   1260
tttccagaag aagaagaagg aggatgtgaa ctgagagtga agttcagcag gagcgcagac   1320 gccccgcgt accagcaggg ccagaaccag ctctataacg agctcaatct aggacgaaga   1380
gaggagtacg atgttttgga caagagacgt ggccgggacc ctgagatggg gggaaagccg   1440
agaaggaaga accctcagga aggcctgtac aatgaactgc agaaagataa gatggcggag   1500
gcctacagtg agattgggat gaaaggcgag cgccggaggg caaggggca cgatggcctt    1560 taccagggtc tcagtacagc caccaaggac acctacgacg cccttcacat gcaggccctg   1620 cccccctcgcg attacaagga tgacgacgat aagtaa                            1656
```

<210> SEQ ID NO 3
<211> LENGTH: 1491
<212> TYPE: DNA
<213> ORGANISM: Artificial Sequence
<220> FEATURE:
<223> OTHER INFORMATION: Synthesized polynucleotide including SEQ ID
      NO:1 and third generation CAR structure

<400> SEQUENCE: 3

```
atggaaattg tgttgacaca gtctccaggc accctgtctt tgtctccagg ggaaacagcc     60
atcatctctt gtcggaccag tcagtatggt tccttagcct ggtatcaaca gaggcccggc    120
caggccccca ggctcgtcat ctattcgggc tctactcggg ccgctggcat cccagacagg    180
ttcagcggca gtcggtgggg gccagactac aatctcacca tcagcaacct ggagtcggga    240
gattttggtg tttattattg ccagcagtat gaatttttg gccaggggac caaggtccag     300
gtcgacatta agcgagaggg cagaggaagt ctgctaacat gcggtgacgt cgaggagaat    360
cctggccagg tgcagctggt gcagtctggg ggtcagatga agaagcctgg cgagtcgatg    420
```

```
agaatttctt gtcgggcttc tggatatgaa tttattgatt gtacgctaaa ttggattcgt      480
ctggcccccg gaaaaaggcc tgagtggatg ggatggctga agcctcgggg ggggccgtc       540 aactacgcac gtccacttca gggcagagtg accatgactc gagacgttta ttccgacaca      600 gccttttttgg agctgcgctc gttgacagta gacgacacgg ccgtctactt ttgtactagg     660
ggaaaaaact gtgattacaa ttgggacttc gaacactggg gccggggcac cccggtcatc      720
gtctcatcag aattcggtgg aggcggttca ggcggaggtg gctctggcgg tggcggatcg      780 tttccccggac cttctaagcc cttttgggtg ctggtggtgg ttggtggagt cctggcttgc     840
tatagcttgc tagtaacagt ggcctttatt attttctggg tgaggagtaa gaggagcagg     900
ctcctgcaca gtgactacat gaacatgact ccccgccgcc ccgggcccac ccgcaagcat     960 taccagcccct atgccccacc acgcgacttc gcagcctatc gctccaaacg ggcagaaag    1020 aaactcctgt atatattcaa acaaccattt atgagaccag tacaaactac tcaagaggaa    1080
gatggctgta gctgccgatt ccagaagaa gaagaaggag gatgtgaact gaagttcagc     1140
aggagcgcag acgccccgc gtaccagcag ggccagaacc agctctataa cgagctcaat     1200
ctaggacgaa gagaggagta cgatgttttg gacaagagac gtggccggga ccctgagatg     1260
gggggaaagc cgcagagaag gaagaaccct caggaaggcc tgtacaatga actgcagaaa    1320
gataagatgg cggaggccta cagtgagatt gggatgaaag cgagcgccg gaggggcaag     1380 gggcacgatg gccttttacca gggtctcagt acagccacca aggacaccta cgacgccctt   1440
cacatgcagg ccctgccccc tcgcgattac aaggatgacg acgataagta a             1491

<210> SEQ ID NO 4
<211> LENGTH: 1521
<212> TYPE: DNA
<213> ORGANISM: Artificial Sequence
<220> FEATURE:
<223> OTHER INFORMATION: Synthesized polynucleotide including SEQ ID
      NO:1 and third generation CAR structure

<400> SEQUENCE: 4
atggaaattg tgttgacaca gtctccaggc accctgtctt tgtctccagg ggaaacagcc       60
atcatctctt gtcggaccag tcagtatggt tccttagcct ggtatcaaca gaggcccggc     120
caggccccca ggctcgtcat ctattcgggc tctactcggg ccgctggcat cccagacagg    180
ttcagcggca gtcggtgggg gccagactac aatctcacca tcagcaacct ggagtcggga    240
gattttggtg tttattattg ccagcagtat gaatttttg gccaggggac caaggtccag     300
gtcgacatta agcgagaggg cagaggaagt ctgctaacat gcggtgacgt cgaggagaat    360
cctggccagg tgcagctggt gcagtctggg ggtcagatga agaagcctgg cgagtcgatg    420
agaatttctt gtcgggcttc tggatatgaa tttattgatt gtacgctaaa ttggattcgt    480
ctggcccccg gaaaaaggcc tgagtggatg ggatggctga agcctcgggg ggggccgtc     540 aactacgcac gtccacttca gggcagagtg accatgactc gagacgttta ttccgacaca    600 gccttttttgg agctgcgctc gttgacagta gacgacacgg ccgtctactt ttgtactagg   660
ggaaaaaact gtgattacaa ttgggacttc gaacactggg gccggggcac cccggtcatc    720
gtctcatcag aattcggtgg aggcggttca ggcggaggtg gctctggcgg tggcggatcg    780 tttccccggac cttctaagcc cttttgggtg ctggtggtgg ttggtggagt cctggcttgc   840
tatagcttgc tagtaacagt ggcctttatt attttctggg tgaggagtaa gaggagcagg    900
ctcctgcaca gtgactacat gaacatgact ccccgccgcc ccgggcccac ccgcaagcat   960
```

```
taccagccct atgccccacc acgcgacttc gcagcctatc gctccggtgg aggcggttca    1020
aaacggggca gaaagaaact cctgtatata ttcaaacaac catttatgag accagtacaa    1080
actactcaag aggaagatgg ctgtagctgc cgatttccag aagaagaaga aggaggatgt    1140
gaactgggcg gtggcggatc gaagttcagc aggagcgcag acgcccccgc gtaccagcag    1200
ggccagaacc agctctataa cgagctcaat ctaggacgaa gagaggagta cgatgttttg    1260
gacaagagac gtggccggga ccctgagatg ggggaaagc cgcagagaag gaagaaccct     1320
caggaaggcc tgtacaatga actgcagaaa gataagatgg cggaggccta cagtgagatt    1380
gggatgaaag gcgagcgccg gaggggcaag gggcacgatg gcctttacca gggtctcagt    1440
acagccacca aggacaccta cgacgccctt cacatgcagg ccctgccccc tcgcgattac    1500
aaggatgacg acgataagta a                                              1521
```

VC-CAR MOLECULE AND USE THEREOF IN REMOVING HIV-1 INFECTED CELLS

CROSS-REFERENCE TO RELATED APPLICATION

This application is a 371 application of International PCT application serial no. PCT/CN2017/072266, filed on Jan. 23, 2017, which claims the priority benefit of Chinese application no. 201610652995.9, filed on Aug. 10, 2016. The entirety of each of the abovementioned patent applications is hereby incorporated by reference herein and made a part of this specification.

BACKGROUND

Technical Field

The present invention relates to the technical field of anti-tumor/and anti-viral infection immunotherapy, and more particularly, to a VC-CAR molecule and a use thereof in removing HIV-1 infected cells.

After infection of Human Immunodeficiency Virus type 1 (HIV-1), a combined antiretroviral therapy (cART) can effectively inhibit virus replication. However, since the virus is integrated into an infected cell and forms a stable latent infection repository, once an infected person stops a cART treatment, viremia will outbreak again in a short time, which constitutes a major obstacle to cure HIV-1 infection.

The current research focus is to activate latent infection virus by specific latency-reversing agents (LRAs), and then the infected cell is killed by drug therapy or induction of an immune system. This intervention strategy is called "shock and kill". However, HIV-1 can mutate rapidly to avoid immune recognition. Researches show that even if the latent infection is successfully activated in the infected person treated by the cART treatment, a $CD8^+$ T lymphocyte in the body cannot completely remove the infected cell due to lack of an effective immune response to HIV-1. Therefore, in the "shock and kill" strategy, in order to better remove the latent infection repository, it is necessary to rebuild a strong immune surveillance function in the body of the infected person.

In recent years, due to characteristics such as high affinity, T cell receptor (TCR) independence and major histocompatibility complex (MHC) non-restriction, an immune cell therapy with chimeric antigen receptor (CAR) becomes a new way to kill tumor cells. CAR is formed by integrating an antibody target region with a T cell activated intracellular signal region, thus giving the cell with a specific antigen recognition ability. By expressing the CAR molecule recognizing natural tumor antigen in an autoimmune cell of a patient and conducting an adoptive immune reinfusion, the tumor cell in the body of the patient can be specifically targeted and killed. The CAR-T cell therapy has been proved to be effective in a clinical treatment of leukemia and lymphoma and has achieved encouraging success. This strategy can also be applied to antiviral treatment, including the treatment of viral infections such as HIV-1, hepatitis B virus (HBV) and hepatitis C virus (HCV). However, the conventionally constructed CAR molecule cannot fully satisfy the immunotherapy of various diseases.

SUMMARY

To overcome the above defects of the prior art, the present invention provides a new CAR molecule, which is called a VC-CAR molecule, and the VC-CAR molecule is formed by linking an HIV-1 broad-spectrum neutralizing antibody VRC01 sourced scFv sequence to an intracellular domain sequence of the conventional CAR molecule, which are respectively used as extracellular and intracellular domains.

Another object of the present invention is to provide a $CD8^+$ T cell modified by the VC-CAR molecule.

Another object of the present invention is to provide a use of the $CD8^+$ T cell modified by the VC-CAR molecule in removing HIV-1 infected cells.

To achieve the objects above, the present invention is realized by the following technical solution.

Use of an HIV-1 broad-spectrum neutralizing antibody VRC01 sourced scFv sequence as shown in SEQ ID NO:1 in serving as an extracellular antigen linking domain of a CAR molecule.

A VC-CAR molecule is formed by linking an HIV-1 broad-spectrum neutralizing antibody VRC01 sourced scFv sequence as shown in SEQ ID NO:1 to an intracellular domain sequence of a CAR molecule, wherein the HIV-1 broad-spectrum neutralizing antibody VRC01 sourced scFv sequence is at an N terminus, and the intracellular domain sequence of the CAR molecule is at a C terminus.

Preferably, a nucleotide sequence of the VC-CAR molecule is as shown in SEQ ID NO:2, SEQ ID NO:3 or SEQ ID NO:4. A structure of the VC-CAR molecule as shown in SEQ ID NO:2 is shown in VR C01-28BBZ-1 in FIG. 1; a structure of the VC-CAR molecule as shown in SEQ ID NO:3 is shown in VR C01-28BBZ-2 in FIG. 1; and a structure of the VC-CAR molecule as shown in SEQ ID NO:4 is shown in VR C01-28BBZ-3 in FIG. 1.

More preferably, a nucleotide sequence of the VC-CAR molecule is as shown in SEQ ID NO:4.

A modified $CD8^+$ T cell is specifically prepared by transducing the VC-CAR molecule designed by the present invention into a $CD8^+$ T cell. A lysis effect of the $CD8^+$ cell modified by the VC-CAR for mediating a cell line expressing gp120 is more obvious.

The present invention further seeks to protect a use of the $CD8^+$ T cell modified by the VC-CAR molecule in removing HIV-1 infected cells.

A modified $CD8^+$ T cell is prepared by a following preparation method: (1) collecting a peripheral blood mononuclear cell, separating and enriching a $CD8^+$ T cell therein, and activating the $CD8^+$ T cell by using anti-CD3, anti-CD28 and IL-2; and (2) after the cell is activated for 48 hours, adding VC-CAR recombinant virus concentrate at a ratio of 1 ml/1×10$^6$ cells for infection, adding a polybrene solution at the same time, and continuing to culture after centrifugation; and after 8 to 12 hours, conducting a second round of virus infection.

Preferably, a concentration of the anti-CD3 is 1 µg/ml, a concentration of the anti-CD28 is 1 µg/ml, and a concentration of the IL-2 is 10 ng/ml.

Preferably, a concentration of the polybrene solution is 8 µg/ml.

A method for amplifying the modified $CD8^+$ T cell by the VC-CAR molecule includes following steps: (1) centrifuging and changing a solution after the $CD8^+$ T cell is infected and modified by a VC-CAR molecule recombinant virus for 12 hours, washing off the virus in a culture medium, resuspending the cell with a fresh culture medium, and adding IL-2 and IL-7 to maintain a cell state; and (2) on the third and fifth day after the virus infection and modification, adding a complete RMPI1640 culture medium to the cell according to the cell state and proliferation, maintaining a cell concentration at 2×10⁶/ml, and supplementing the IL-2 and IL-7 to continue culturing and passage in time, so as to further amplify the cell.

Preferably, a concentration of the IL-2 is 10 ng/ml and a concentration of the IL-7 is 10 ng/ml.

Compared with the prior art, the present invention has the following beneficial effects.

The newly modified VC-CAR-T cell in the present invention is co-cultured with a cell line expressing HIV-1 envelope protein or an HIV-1 infected CD4⁺ T cell, and the VC-CAR-T cell can be specifically activated and secrete a great number of cytotoxicity-related cytokines (including IFN-γ and Granzyme B), thereby strongly mediating lysis of a target cell.

Compared with the reported CD4-CAR-T cell, the lysis effect of the newly modified VC-CAR-T cell in the present invention for mediating a cell line expressing gp120 is more obvious and potent.

The IL-2+IL-7 cytokine combination used in the present invention can further improve amplification times of the CD8⁺ T cell of the HIV-1 infected patient in comparison with the conventional amplification method of applying the IL-2 alone.

DESCRIPTION OF THE EMBODIMENTS

The present invention is further described in detail in combination with the accompanying drawings of the specification and the detailed embodiments, and the embodiments are merely intended to explain the present invention, but are not intended to limit the scope of the present invention. Unless otherwise specified, experiment methods used in the following embodiments are all conventional methods. Unless otherwise specified, all materials and reagents used are the materials and reagents that can be obtained from commercial sources.

Embodiment 1

Figure 1:
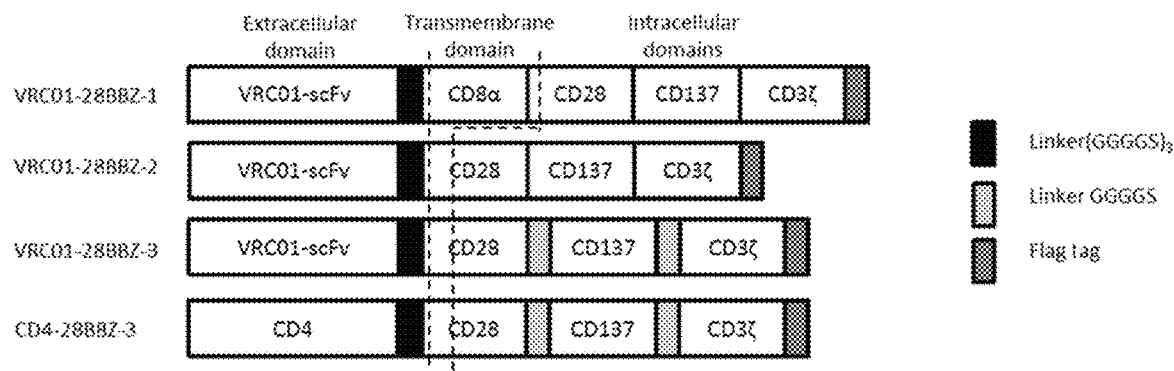
FIG. 1 is a structural schematic diagram of a constructed VC-CAR molecule.

A nucleotide sequence of a VC-CAR molecule with VRC01 as an extracellular antigen linking domain is as shown in SEQ ID NO:2, SEQ ID NO:3 or SEQ ID NO:4. A structure of the VC-CAR molecule as shown in SEQ ID NO:2 is shown in VR C01-28BBZ-1 in FIG. 1; a structure of the VC-CAR molecule as shown in SEQ ID NO:3 is shown in VR C01-28BBZ-2 in FIG. 1; and a domain of the VC-CAR molecule as shown in SEQ ID NO:4 is shown in VR C01-28BBZ-3 in FIG. 1.

An HIV-1 broad-spectrum neutralizing antibody VRC01 sourced scFv sequence is as shown in SEQ ID NO:1.

A structure design of the VC-CAR molecule according to the present invention is described in details hereinafter using the VC-CAR molecule as shown in SEQ ID NO:4. An N' end of the sequence of the VC-CAR molecule is the HIV-1 broad-spectrum neutralizing antibody VRC01 sourced scFv sequence, which can be specifically linked to a CD4 linking domain of a virus envelope protein; a C' end of the sequence of the VC-CAR molecule is based on a third generation CAR structure, which is formed by linking intracellular domains including CD28 (nucleotides 460-660, GenBank NM_006139.3), CD137 (nucleotides 640-765, GenBank NM_001561.5) and CD3ζ (nucleotides 160-492, GenBank NM_198053.2) in series, and the scFv and a intracellular signal molecule are linked by a transmembrane domain of the CD28 molecule.

Embodiment 2

Figure 2:
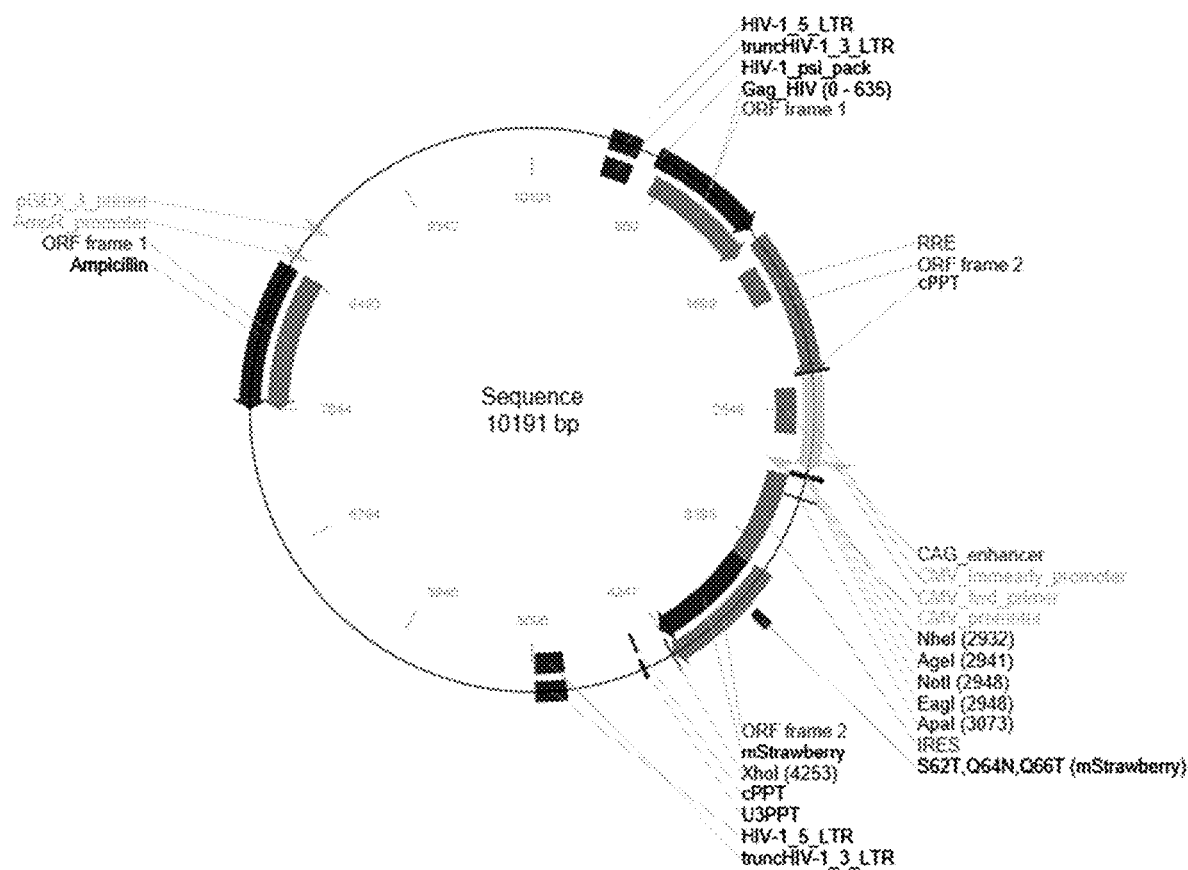
FIG. 2 is a structural schematic diagram of a pCPPT-IRES-mStrawberry lentivirus vector.

I. A VC-CAR molecule recombinant pCPPT-IRES-mStrawberry lentivirus vector: a VC-CAR was synthesized according to a sequence as shown in SEQ ID NO:4, the synthesized VC-CAR was inserted into the pCPPT-IRES-mStrawberry lentivirus vector by double enzyme digestion of NheI and NotI (see FIG. 2), to obtain the VC-CAR molecule recombinant pCPPT-IRES-mStrawberry lentivirus vector, wherein specific steps of the enzyme digestion and linking may be referred to a conventional method in this art.

A growing HEK293T cell was evenly spread in a 10 cm culture dish treated with polylysine (cell density was about 6.5×10⁴/cm²), wherein single uniform distribution of the cell was required. After the cell was cultured for about 24 hours, a cell confluency should be close to 80%; at the moment, the solution in each dish was exchanged with 12 ml complete culture medium, and meanwhile, 3.75 μl chloroquine (100 mM, 4000×) was added. After changing the solution, a calcium phosphate-DNA mixed solution was prepared according to Table 1, the mixed solution was allowed to stand for one minute after being turned upside down for several times to be mixed evenly, then was quickly added into the cell culture solution of each dish by 3 ml/dish, the mixed solution was shaken up while adding, and was added drop by drop quickly.

TABLE 1

| Formula of Phosphate-DNA Mixed Solution System | |
|---|---|
| CaCl₂ solution (2.5M) | 600 μl |
| pCPPT recombined by VC-CAR molecule | 54 μg |
| psPAX2 | 66 μg |
| pMD2G | 30 μg |
| Add sterile water until a final volume is 6000 μl | |
| HeBS solution (2×) | 6000 μl |

12 hours after transfection, a cell confluency should be close to 100%; at the moment, the solution in each dish was exchanged with 12 ml fresh culture medium, and meanwhile, 90 μl sodium butyrate (1 M, 100×) was added. About 48 hours after transfection, all 34 ml HEK293T cell supernatants were collected, filtered by a 0.45 μm filter and fed into a 50 ml centrifuge tube. A PEG-NaCl-PBS mixed solution was added according to a ratio shown in Table 2 below; after being turned upside down to be mixed evenly, the mixture was allowed to stand at 4° C. for 1.5 hours, and during this period, the mixture was allowed to stand at 4° C. overnight after being mixed evenly for one time every 20 to 30 minutes or was turned upside down to be mixed evenly.

TABLE 2

| Culture medium | 12 ml |
|---|---|
| 50% (m/v) PEG6000 | 3 ml |
| 4M NaCl | 1.28 ml |
| PBS | 1.37 ml |

The mixed solution was centrifuged at 4° C. and 7000 g for 10 minutes, white precipitate could be seen on a wall of the tube, all supernatants were carefully removed, a proper volume (300 μl to 3 ml) of fresh culture medium was added, and the mixture was gently shaken to dissolve the precipitate, thus obtaining a VC-CAR molecule recombinant virus concentrated solution, which was used immediately or sub-packaged and then stored at −80° C.

II. Expression of VC-CAR in a $CD8^+$ T cell: peripheral blood mononuclear cells were separated from a peripheral blood sample, and then $CD8^+$ T lymphocytes were separated and enriched by a CD8 antibody coupled with biotin, and then counted and centrifuged. The lymphocytes were suspended by a RPMI1640 complete culture medium, and then uniformly spread into a cell culture plate at a cell concentration of $2\times10^6$/ml. Anti-CD3 (final concentration was 1 μg/ml), anti-CD28 (final concentration was 1 μg/ml) antibody and IL2 (final concentration was 10 ng/ml) were used to stimulate the lymphocytes; after 48 hours, the lymphocytes were collected for pseudovirus infection.

Figure 3:
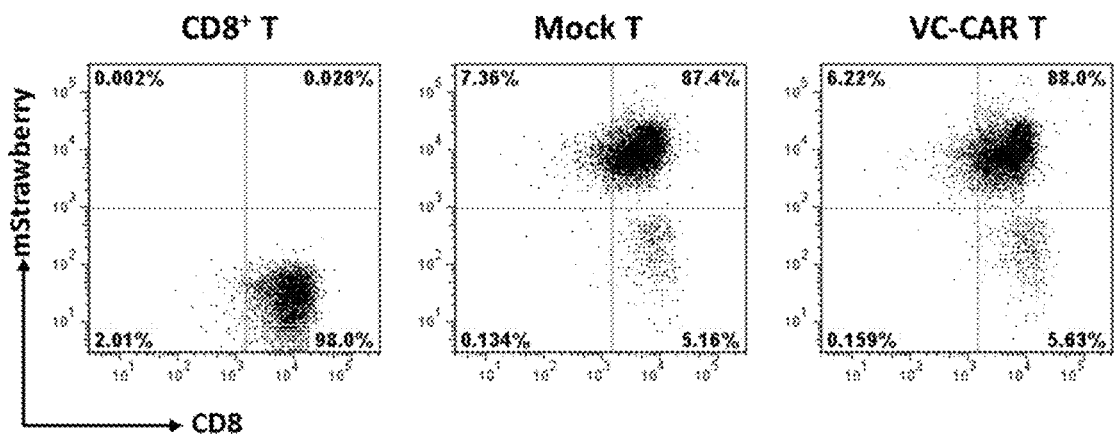
FIG. 3 illustrates an expression of the VC-CAR in a CD8⁺ T cell.

A proper amount of target cell suspension in good growth state was taken and put into a centrifuge tube for centrifugation at 300 g for 5 minutes. A supernatant was discarded, the pseudovirus concentrated solution was added at a cell ratio of $1$ ml/$1\times10^6$, and polybrene with a final concentration of 8 μg/ml was added at the same time, and then the mixture was gently blown and mixed. The cell suspension was transferred to a culture dish, and centrifuged at 37° C. and 350×g for 90 minutes; after centrifugation, the cell suspension was returned to an incubator for further culture. After about 8 to 12 hours, second round of infection was carried out, and the steps were the same as above. After about 12 hours, centrifugation and solution change were carried out, the virus in the culture medium was washed off with PBS, the cells were suspended by a fresh culture medium, and IL-2 and IL-7 both with a final concentration of 10 ng/ml were added to maintain the cell state. The cells were continuously cultured and timely passaged to further amplify the cells. On the third day after infection, a complete RMPI1640 culture medium was added to the cells according to the cell state and proliferation, and the cell concentration was maintained at $2\times10^6$/ml. Moreover, IL-2 and the IL-7 were supplemented, the final concentrations of which were both 10 ng/ml. On the fifth day after infection, the cells were continuously amplified according to the procedure of the third day. Flow cytometry was used to detect expression of a fluorescent protein mStrawberry to determine an infection rate of the VC-CAR, and the infection rate should usually reach more than or equal to 50% (FIG. 3). On the fifth day after infection, the cells were used for subsequent experimental detection or continued culture and cryopreservation. For convenience, they were called VC-CAR-T cells for all the following experiments hereinafter.

Embodiment 3

Figure 4:
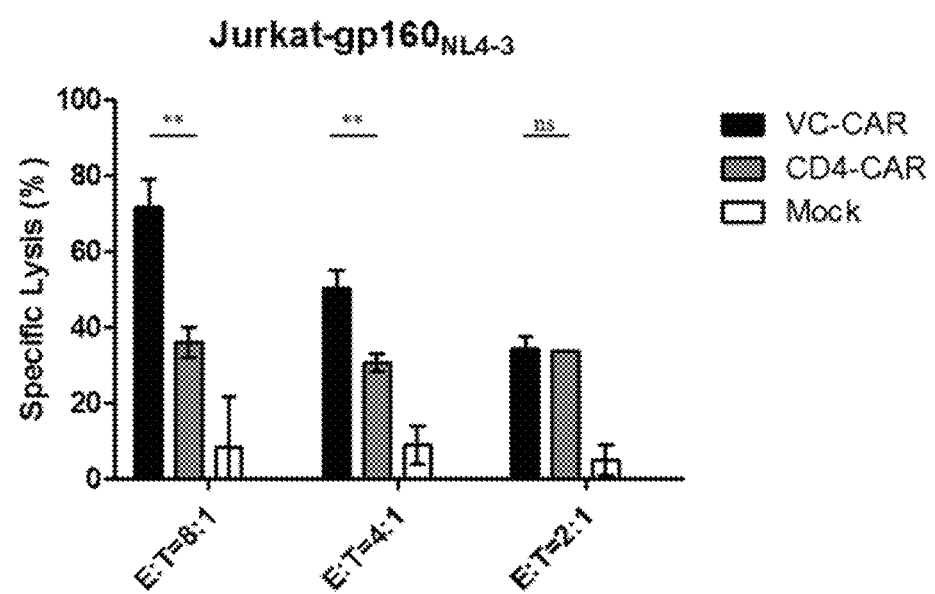
FIG. 4 illustrates a comparison of killing effects after CD8⁺ T cells modified by the VC-CAR and a CD4-CAR are respectively mixed with a target cell line.

I. Comparison of killing effects after $CD8^+$ T cells modified by a VC-CAR and a CD4-CAR were respectively mixed with a target cell line: earlier study used an extracellular domain of the CD4 molecule as a basis to construct a CAR-T cell (CD4-CAR-T cell). Since the CD4 molecule was a natural receptor of a HIV-1 envelope glycoprotein gp120, the CD4-CAR-T cell could lyse a target cell expressing gp120. To compare the effects of a VC-CAR-T cell and a CD4-CAR-T cell, CD4-CAR was constructed by replacing a scFv sequence of the VC-CAR with an extracellular domain of the CD4 molecule according to previous reports. A $CD8^+$ T lymphocyte was transduced under the same condition, and then mixed with a target cell line expressing HIV-1 envelope protein (Jurkat-gp160$_{NL4-3}$) to carry out a cell killing experiment in 96-well plate with a U-shaped bottom. The number of the target cells was $10^4$/well, and a volume of a RMPI1640 complete culture medium was 200 μl/well. Within a given effector-target ratio range (8:1 to 2:1), after 24 hours, the killing activity of the modified $CD8^+$ T lymphocyte in each experimental group was determined by detecting the release of lactate dehydrogenase. The results showed that: the VC-CAR-T cell had a stronger target cell lysis ability than that of the CD4-CAR-T cell. The possible reason for the results was that the HIV-1 broad-spectrum neutralizing antibody sourced scFv had a stronger affinity for HIV-1 gp120 than that of the natural CD4 molecule (see FIG. 4).

Figure 5:
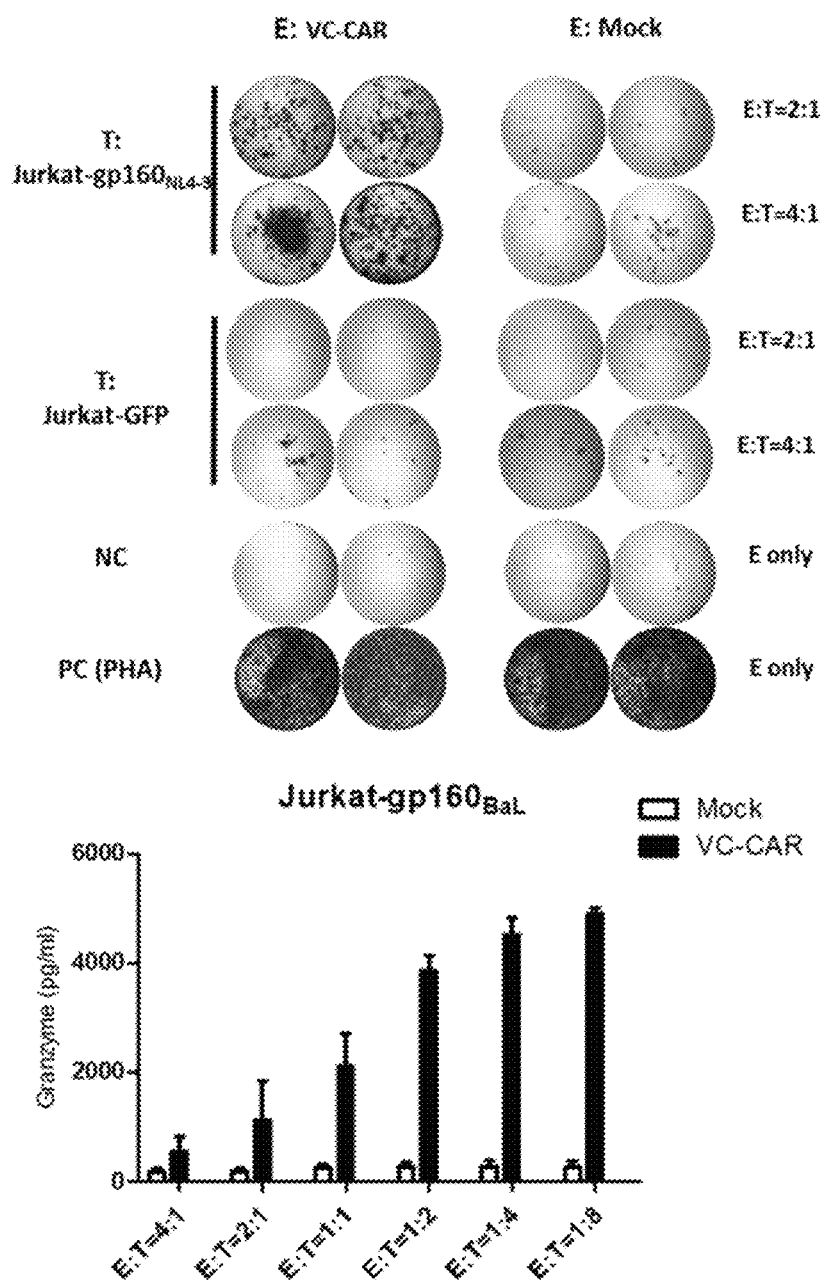
FIG. 5 illustrates a secretion of IFN-γ and Granzyme-B after a mixed culture of a VC-CAR-T cell and a target cell line expressing HIV-1 envelope proteins.

II. Secretion of specific cytokines after mixed culture of a VC-CAR-T cell and a target cell line expressing HIV-1 envelope proteins: to further detect the function of the VC-CAR, a mixed culture was carried out to the VC-CAR-T cell and the cell line Jurkat-gp160$_{NL4-3}$ expressing HIV-1 envelope proteins in a 96-well PVDF plate pre-coated with an IFN-γ antibody, the number of effector cells was $10^4$/well; within a given effector-target ratio range (4:1 and 2:1), after 24 hours, the IFN-γ secretion of the VC-CAR-T cell was detected by ELIspot experiment. The results showed that: the IFN-γ secretion of the VC-CAR-T cell mixed with two target cells was significantly increased, while the VC-CAR-T cell mixedly cultured with a control cell line Jurkat-GFP negative to the HIV-1 envelope protein did not secrete IFN-γ. On the other hand, the control effector cell mixedly cultured with the target cell line expressing HIV-1 envelope proteins had no obvious IFN-γ secretion, thus further proving that the IFN-γ secretion was specific to the VC-CAR-T cell (FIG. 5).

The VC-CAR-T cell and the Jurkat-gp160$_{NL4-3}$ were mixedly cultured for 24 hours respectively; within a given effector-target ratio range (4:1 to 2:1), the ELISA experiment of granzyme B also showed that with the increase of the target cells (Jurkat-gp160$_{NL4-3}$), the cytokine secretion of the VC-CAR-T cell would increase in a dose-dependent manner, while the control target cell (Jurkat-GFP) would not stimulate the VC-CAR-T cell to secrete the IL-2 and the granzyme B. The results showed that the VC-CAR-T cell had an ability to secrete antiviral cytokines efficiently under the stimulation of the specific antigen (FIG. 5).

Figure 6A:
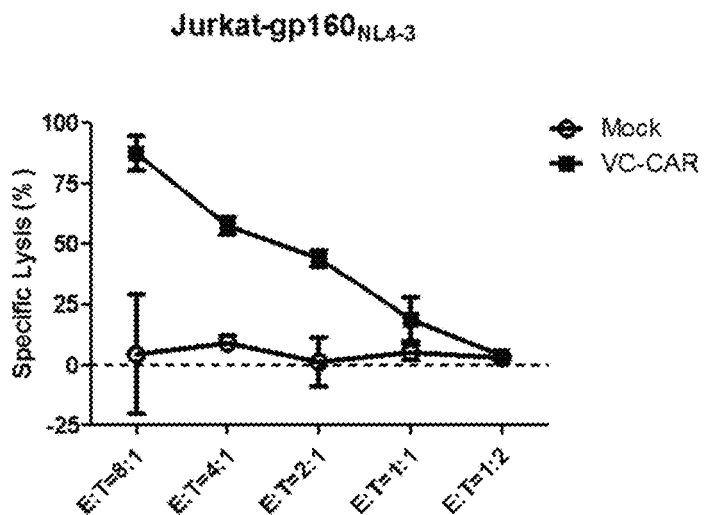
FIG. 6A to FIG. 6C illustrate a detection of a killing activity of the VC-CAR-T cell by detecting LDH release after the mixed culture of the VC-CAR-T cell and the target cell line expressing HIV-1 envelope proteins.
Figure 6B:
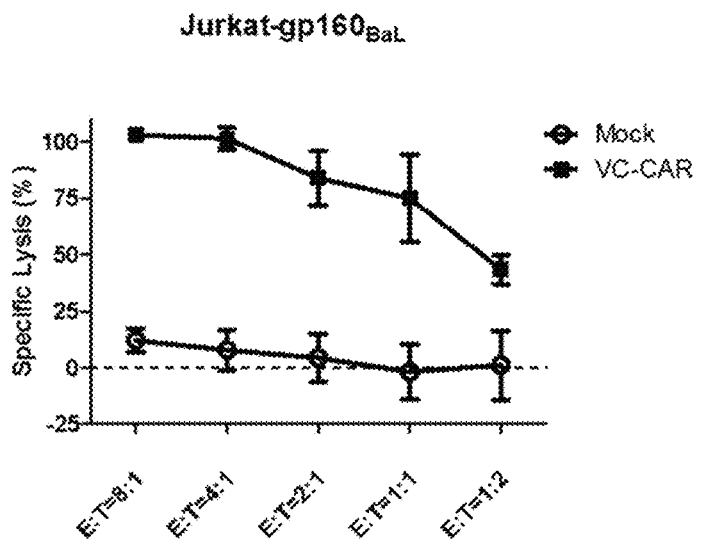
Figure 6C:
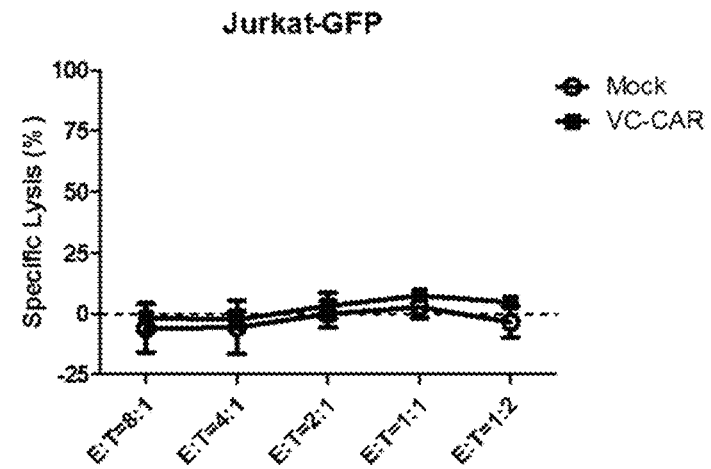

III. Detection of a killing activity after mixed culture of a VC-CAR-T cell and a target cell line expressing HIV-1 envelope proteins: to further detect the function of the VC-CAR, the VC-CAR-T cell was mixedly cultured with two cell lines Jurkat-gp160$_{NL4-3}$ and Jurkat-gp160$_{BaL}$ expressing HIV-1 envelope proteins respectively, and a cell killing experiment was carried out in a 96-well plate with a U-shaped bottom. The number of the target cells was $10^4$/well, and a volume of a RMPI1640 complete culture medium was 200 μl/well. Within a given effector-target ratio range (8:1 to 0.5:1), after 24 hours, cytotoxicity of the VC-CAR-T cell to the cell expressing HIV-1 envelope proteins was detected by LDH release. The results showed that: the VC-CAR-T cell significantly killed two target cells (Jurkat-gp160$_{NL4-3}$ and Jurkat-gp160$_{BaL}$) expressing HIV-1 gp120 in a dose-dependent manner in the effector-target ratio range from 8:1 to 0.5:1, while the control target cell (Jurkat-GFP) had no significant killing effect, which indicated that the killing effect of the VC-CAR-T cell on the target cell was specific to HIV-1 gp120. No matter the Jurkat-gp160$_{NL4-3}$ and the Jurkat-gp160$_{BaL}$ or the control target cell Jurkat-GFP, the the control effector cells did not show obvious killing effect, thus further illustrating the effect specificity of the VC-CAR-T cell (FIG. 6A to FIG. 6C).

Figure 7A:
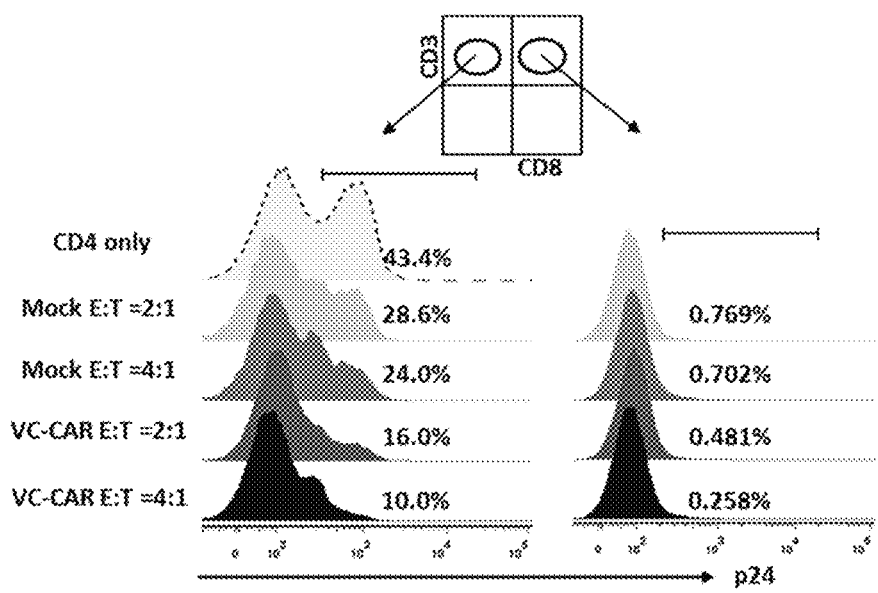
FIG. 7A to FIG. 7B illustrate a detection of a ratio of Gag⁺ CD4⁺ T lymphocyte by flow cytometry after a mixed culture of the VC-CAR-T cell and a CD4⁺ T lymphocyte infected by wild-type HIV-1$_{NL4-3}$ to verity a killing activity of the VC-CAR-T cell.
Figure 7B:
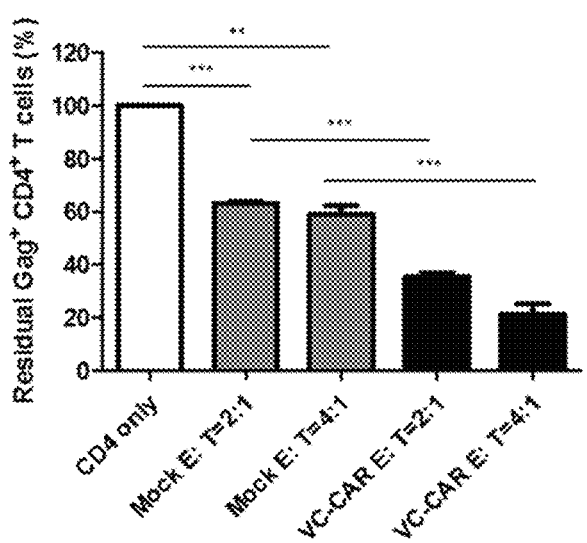

IV. Detection of a killing activity after mixed culture of a VC-CAR-T cell and a CD4$^+$ T lymphocyte infected by wild-type HIV-1$_{NL4-3}$: to further prove the effectiveness of the VC-CAR-T cell in removing the wild-type HIV-1 infected cells, and the wild-type HIV-1$_{NL4-3}$ was used to infect a CD4$^+$ T lymphocyte isolated from a blood sample of a healthy person. During infection, a volume of a RMPI1640 complete culture medium was 1 ml/well (24-well plate), containing $2 \times 10^6$ cells, and corresponding to 200 ng (p24) wild-type virus. A solution was changed 3 hours after infection. On the eighth day after infection, the cell was mixed with a homologous CD8$^+$ T lymphocyte modified by the VC-CAR in ratios of 1:2 and 1:4, and a cell killing experiment was carried out in a 24-well plate. A number of the target cells was $10^6$/well, and a volume of a RMPI1640 complete culture medium was 500 μl/well. After 48 hours, a ratio of the Gag$^+$ CD4$^+$ T lymphocyte was detected by flow cytometry to verify the killing effect of the VC-CAR-T cell. The results showed that: a removal rate of the VC-CAR-T cell to the HIV-1 infected cells was as high as 78%, showing a significant killing effect, while a value of control effector cells was less than 30%, and a difference of the two was statistically significant (FIG. 7A to FIG. 7B).

What is claimed is:

1. A use of an HIV-1 broad-spectrum neutralizing antibody VRC01 sourced scFv sequence shown in SEQ ID NO:1 in serving as an extracellular antigen linking domain of a CAR molecule.

2. A VC-CAR molecule, wherein the VC-CAR molecule is formed by linking an HIV-1 broad-spectrum neutralizing antibody VRC01 sourced scFv sequence as shown in SEQ ID NO:1 to an intracellular domain sequence of a CAR molecule, the HIV-1 broad-spectrum neutralizing antibody VRC01 sourced scFv sequence is at an N terminus, and the intracellular domain sequence of the CAR molecule is at a C terminus.

3. The VC-CAR molecule according to claim 2, wherein a nucleotide sequence of the VC-CAR molecule is as shown in SEQ ID NO:2, SEQ ID NO:3 or SEQ ID NO:4.

4. The VC-CAR molecule according to claim 2, wherein a nucleotide sequence of the VC-CAR molecule is as shown in SEQ ID NO:4.

5. A modified $CD8^+$ T cell, wherein the modified CD8+ T cell is prepared by transducing the VC-CAR molecule according to claim 2 into a $CD8^+$ T cell.

6. A use of the modified $CD8^+$ T cell according to claim 5 in preparing a formulation for removing HIV-1 infected cells.

7. The modified $CD8^+$ T cell according to claim 5, wherein the modified CD8+ T cell is prepared by a following method: (1) collecting a peripheral blood mononuclear cell, separating and enriching a $CD8^+$ T cell therein, and activating the $CD8^+$ T cell by using anti-CD3, anti-CD28 and IL-2; and (2) after the cell is activated for 48 hours, adding a VC-CAR molecule recombinant virus concentrate at a ratio of 1 ml/1×10$^6$ cells for infection, adding a polybrene solution at the same time, and continuing to culture after centrifugation; and after 8 to 12 hours, conducting a second round of virus infection.

8. The modified $CD8^+$ T cell according to claim 7, wherein a concentration of the anti-CD3 is 1 µg/ml, a concentration of the anti-CD28 is 1 µg/ml, and a concentration of the IL-2 is 10 ng/ml.

9. A method for amplifying the modified $CD8^+$ T cell according to claim 5, characterized by comprising following steps: (1) centrifuging and changing a solution after the $CD8^+$ T cell is infected and modified by a VC-CAR molecule recombinant virus for 12 hours, washing off the virus in a culture medium, resuspending the cell with a fresh culture medium, and adding IL-2 and IL-7 to maintain a cell state; and (2) on the third day and the fifth day after the virus infection and modification, adding a complete RMPI1640 culture medium to the cell according to the cell state and proliferation, maintaining a cell concentration at 2×10$^6$/ml, and supplementing the IL-2 and IL-7 to continue culturing and passage in time, so as to further amplify the cell.

10. The method according to claim 9, wherein a concentration of the IL-2 is 10 ng/ml and a concentration of the IL-7 is 10 ng/ml.

11. A modified $CD8^+$ T cell, wherein the modified CD8+ T cell is prepared by transducing the VC-CAR molecule according to claim 3 into a $CD8^+$ T cell.

12. A modified $CD8^+$ T cell, wherein the modified CD8+ T cell is prepared by transducing the VC-CAR molecule according to claim 4 into a $CD8^+$ T cell.

13. A method for amplifying the modified $CD8^+$ T cell according to claim 7, characterized by comprising following steps: (1) centrifuging and changing a solution after the $CD8^+$ T cell is infected and modified by a VC-CAR molecule recombinant virus for 12 hours, washing off the virus in a culture medium, resuspending the cell with a fresh culture medium, and adding IL-2 and IL-7 to maintain a cell state; and (2) on the third day and the fifth day after the virus infection and modification, adding a complete RMPI1640 culture medium to the cell according to the cell state and proliferation, maintaining a cell concentration at 2×10$^6$/ml, and supplementing the IL-2 and IL-7 to continue culturing and passage in time, so as to further amplify the cell.

14. A method for amplifying the modified $CD8^+$ T cell according to claim 8, characterized by comprising following steps: (1) centrifuging and changing a solution after the $CD8^+$ T cell is infected and modified by a VC-CAR molecule recombinant virus for 12 hours, washing off the virus in a culture medium, resuspending the cell with a fresh culture medium, and adding IL-2 and IL-7 to maintain a cell state; and (2) on the third day and the fifth day after the virus infection and modification, adding a complete RMPI1640 culture medium to the cell according to the cell state and proliferation, maintaining a cell concentration at 2×10$^6$/ml, and supplementing the IL-2 and IL-7 to continue culturing and passage in time, so as to further amplify the cell.

* * * * *